United States Patent [19]

Laughlin et al.

[11] 4,355,643
[45] Oct. 26, 1982

[54] VACUUM CUP DOPPLER FLOW TRANSDUCER AND METHOD FOR USING SAME

[75] Inventors: Donald E. Laughlin; Paul J. Krumm, both of West Branch, Iowa

[73] Assignee: University of Iowa Research Foundation, Iowa City, Iowa

[21] Appl. No.: 127,370

[22] Filed: Mar. 5, 1980

[51] Int. Cl.³ .................................. A61B 10/00
[52] U.S. Cl. ............................................. 128/663
[58] Field of Search ..................... 128/632–633, 128/637, 643, 645–649, 660–663, 667, 669, 691–694, 672, 736, 745–746, 748, 752; 73/194 A

[56] References Cited

U.S. PATENT DOCUMENTS

| | | | |
|---|---|---|---|
| 3,545,260 | 12/1970 | Lichtenstein et al. | 128/647 |
| 3,568,663 | 3/1971 | Phipps | 128/643 |
| 3,661,146 | 5/1972 | Peronneau et al. | 128/663 |
| 4,097,835 | 6/1978 | Green | 128/663 |

FOREIGN PATENT DOCUMENTS

| | | | |
|---|---|---|---|
| 2730574 | 2/1978 | Fed. Rep. of Germany | 128/736 |
| 1398022 | 6/1975 | United Kingdom | 128/663 |

*Primary Examiner*—Robert W. Michell
*Assistant Examiner*—Francis J. Jaworski
*Attorney, Agent, or Firm*—Zarley, McKee, Thomte, Voorhees & Sease

[57] ABSTRACT

The present invention comprises a vacuum cup having a concave undersurface on which is mounted a doppler flow transducer. A vacuum tube is in communication with the undersurface of the cup and is capable of removing the air from beneath the suction cup so as to permit the suction cup to be clamped over an artery or other vessel. The device is used by activating the transducer to cause it to transmit a sound signal into the artery. The secondary or echo sounds created by this sound signal are sensed by the transducer and the transducer converts these secondary sound signals into electrical signals which are transmitted to means for analyzing the signals so as to determine the velocity of fluid flow within the vessel.

17 Claims, 7 Drawing Figures

U.S. Patent    Oct. 26, 1982    4,355,643
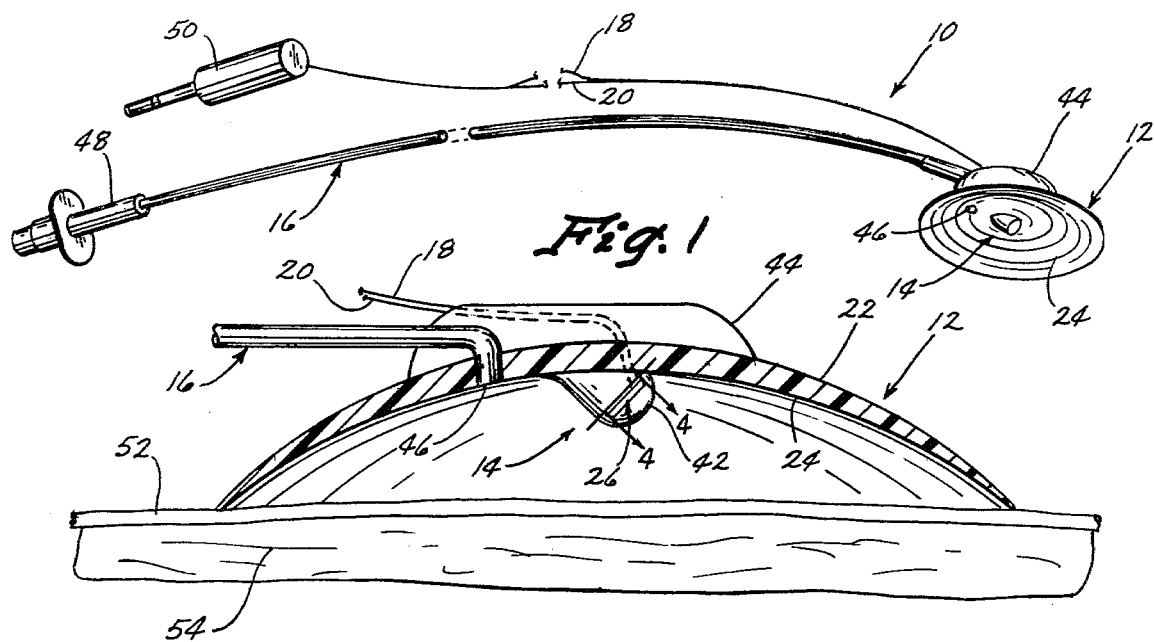
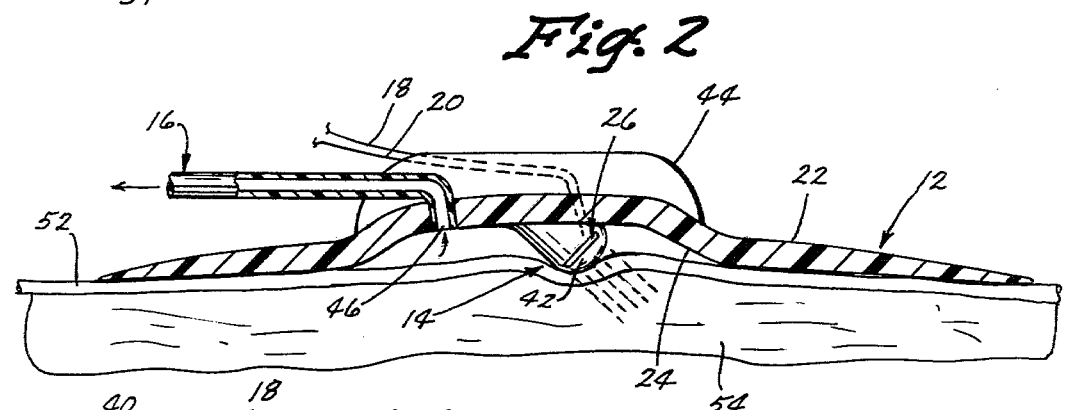
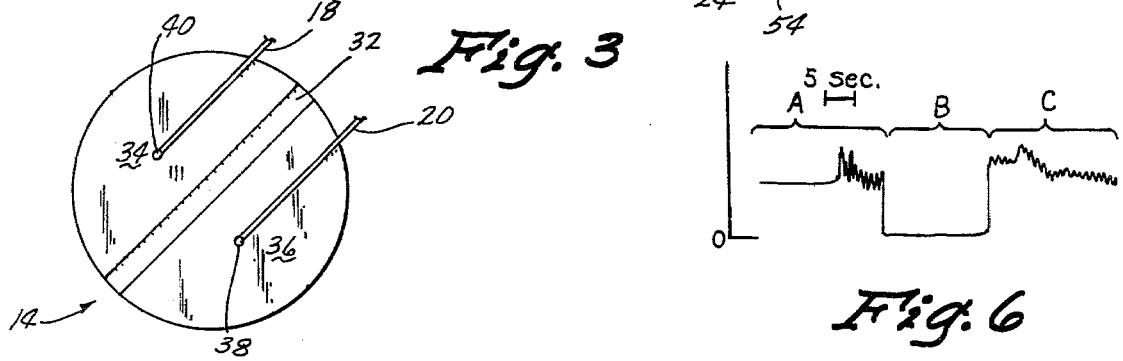
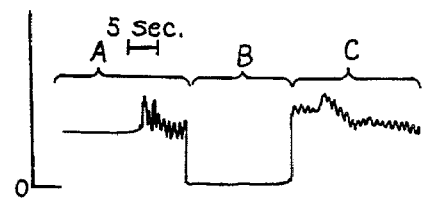
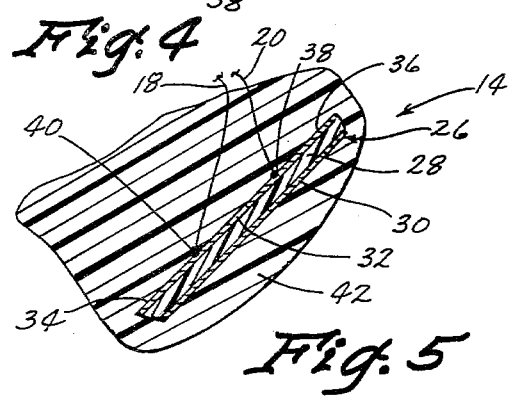
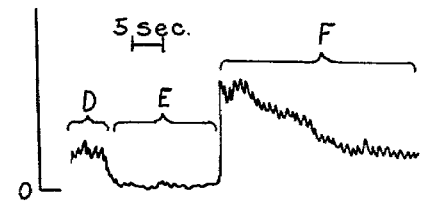

VACUUM CUP DOPPLER FLOW TRANSDUCER AND METHOD FOR USING SAME

BACKGROUND OF THE INVENTION

The present invention relates to a device for sensing the velocity of fluid flow in human and animal vessels, and to the method for using this device.

One problem which surgeons encounter in coronary bypass surgery is the difficulty in determining the precise velocity of the blood in any given vessel. Prior to the present invention there were three methods known for measuring the flow or velocity of blood in any coronary artery. One method involved the measuring of coronary flow by placing an electromagnetic flow meter around one of the primary coronary arteries at the time of cardiac surgery. This method was unsatisfactory, however, inasmuch as it required surgical dissection of the coronary vessel. Furthermore, this method could be used on only the right coronary system of the heart and could not be used on the left coronary system.

Another method for measuring coronary velocity involves the attaching of a doppler crystal to the end of a catheter placed in the left or right main coronary arteries, or in the coronary sinus. This particular method was unsatisfactory because it did not permit the measuring of velocity in the smaller branches of the coronary vessels. The method involved a large catheter and the catheter could only be inserted in the larger vessels.

Another method for measuring flow within the coronary arteries involved the placement of electromagnetic flow meters on coronary bypass grafts during cardiac surgery. This approach, however, complicated the surgery and did not always produce satisfactory results. Furthermore, the time involved in surgery for this process, was substantial.

Therefore, a primary object of the present invention is the provision of an improved device for sensing the velocity of fluid flow in human and animal vessels.

A further object of the present invention is the provision of a device and method which permits measurements of fluid velocity or flow to be taken in a comparatively short time.

A further object of the present invention is the provision of a device and method which minimizes the electrical hazards to the patient at the time the measurements are being taken.

A further object of the present invention is the provision of a method and device which minimizes the potential tissue damage to the patient during the measurement.

A further object of the present invention is the provision of a method and device which permits the measurement of fluid velocity within the vessel while at the same time minimizing the impairment of the functioning of the organ involved.

Another object of the present invention is the provision of a device which can be quickly placed in operative position on the patient, and then can be moved to another location for a second reading or a plurality of readings in a comparatively short time.

A further object of the present invention is the provision of a device which is small so as to minimize interference with other instruments and so as to be capable of use in small, hard to get at locations.

A further object of the present invention is the provision of a device which is economical to manufacture, reliable in use, and simple to operate.

SUMMARY OF THE INVENTION

The present invention comprises a soft, pliable suction cup made of a bio-compatible plastic such as silicone rubber with a doppler flow transducer mounted under its bottom surface. A vacuum line is attached to the suction cup in such a manner to permit air to be withdrawn from beneath the cup.

The device can be placed on the exposed heart of a patient about to undergo coronary bypass surgery. With the transducer held against the surface of the heart, the amount of constriction in a given coronary artery can accurately be assessed during normal function of the heart before the patient is put on cardio-pulmonary bypass.

With the present invention, surgeons can make an accurate quantitative analysis of the necessity for bypass on a given coronary artery. They presently must depend on angiographic evidence acquired during cardiac catheterization. This latter evidence, although it is the best available, can be difficult to quantitate because of the fact that constrictions vary both in cross-sectional shape and length. In addition, correlation of angiographic films with surface characteristics of the human heart is on occasion difficult.

The use of the present invention has given consistently reliable signals under operating room conditions during clinical experimental studies. The major clinical use of this invention has been to confirm angiographic data in the operating room prior to coronary bypass procedure. With the flow probe attached to the myocardium of the patient above the coronary artery in question, the artery is occluded, or shut off, for approximately 2-20 seconds with forceps or other instruments. The probe senses the changes in velocity of fluid passing through the artery prior to, during, and immediately after the occlusion. If fluid is passing through the vessel properly, the flow will increase dramatically when the temporary occlusion is terminated. The more the vessel itself is permanently occluded, the less dramatic is the rebound of flow after the artificial occlusion. At a high percentage of permanent occlusion in the vessel, there is no rebound at all. Flow simply returns to the value prior to shutting off the vessel. This procedure gives highly reliable, quantitative data on the extent of occlusion in the artery and in questionable cases can determine in a more reliable way than present state of the art devices, the necessity for a coronary bypass.

While the device has heretofore been primarily used for coronary bypass surgery, it may be used for other purposes also. The device is capable of measuring the velocity of the fluid within the vessel, and could be used throughout the human body to make such determinations.

BRIEF DESCRIPTION OF THE FIGURES OF THE DRAWINGS

FIG. 1 is a perspective view of the device of the present invention.

FIG. 2 is an enlarged sectional view of the device placed over an artery.

FIG. 3 is a view similar to FIG. 2, but showing the suction cup of the present invention in a collapsed position.

FIG. 4 is a sectional view taken along line 4—4 of FIG. 2.

FIG. 5 is a sectional view of the transducer and lens showing the transducer and lens in the same orientation as shown in FIGS. 2 and 3.

FIG. 6 is a reproduction of a graph showing the velocity characteristics of an occluded vessel as measured by the present device.

FIG. 7 is a graph similar to FIG. 6, but showing the velocity characteristics of a normal non-occluded vessel.

DETAILED DESCRIPTION OF THE INVENTION

Referring to the drawings, the numeral 10 refers to the device of the present invention which is referred to as a probe. Probe 10 comprises a suction cup 12, a transducer assembly 14, a vacuum tube 16 and a pair of electrical leads 18, 20. Suction cup 12 is comprised of a biocompatible plastic preferably silicone rubber, having a convex upper surface 22 and a concave undersurface 24. Suction cup 12 is preferably cast in a lucite mold with two-part medical grade elastomer. The preferred elastomer for use in this invention is MDX 4-4210 with catalyst, manufactured by Dow Corning of Midland, Michigan. The curing of the cup is accomplished with an hour exposure 5 centimeters from a 100 watt bulb or equivalent heat source. While the size of the cup may vary, the preferred size is 27 millimeters in diameter, 1.25 millimeters thick at the apex, tapering to zero thickness at the circumference, and with a maximum depth of the cup being 3 millimeters.

Transducer assembly 14 is mounted in the center of cup 12 on the undersurface thereof. Assembly 14 is comprised of an epoxy material which is dielectric and which is capable of transmitting sound by conduction. An example of a compound which will work for the epoxy of the transducer assembly 14 is a biocompatible epoxy No. 795 Medical Grade Resin and No. 796 Hardener, manufactured by Hysol Corporation, Olean, New York.

Embedded within the epoxy is a transducer 26 which is comprised of a circular disc crystal made of piezoelectric material designated by the numeral PZT-5A, manufactured by Valtec Corporation, Hopkinton, Massachusetts. This crystal is approximately one to two millimeter in diameter and includes gold plate on the outer surfaces of both opposite sides as is illustrated in FIG. 5. The crystal disc is designated by the numeral 28 and the numeral 30 designates the gold plate on the lower surface of disc 28.

The gold plate on the top of disc 28 is divided by a scratch 32 into two half circle plates 34, 36. Scratch 32 disconnects half circle plate 34 from half circle plate 36 so that the two are electrically separated from one another.

Leads 18, 20 are connected to discs 34, 36 by means of solder connections 38, 40. In the place of these solder connections, an electrically conductive glue or cement could be used, such glues being well known in the art.

Transducer 26 is completely embedded within an epoxy lens designated by the numeral 42. This epoxy is capable of transmitting sound, but is dielectric. The preferred compound for this epoxy is No. 795 Medical Grade Resin and No. 796 Hardener, manufactured by Hysol Corporation, Olean, New York. The epoxy is formed into a hemispherical lens 42.

As can be seen in FIGS. 2 and 3, transducer 26 is disposed at a 45° angle with respect to the plane defined by the peripheral edge of cup 12. This is the preferred angle of disposal for transducer 26. The angle of disposal of transducer 26 affects the electronic circuitry required to analyze the signals transmitted and received by transducer 26. Therefore, if the angle is changed from 45°, appropriate adjustments must be made in the device for analyzing the circuit (not shown). Leads 18, 20 extend upwardly from transducer 26 through the silicone of cup 12 and further through a silicone hub 44 above suction cup 12.

Vacuum tube 16 extends through hub 44 and suction cup 12 to an inner end 46 which is in communication with the space beneath suction cup 12. On the other end of vacuum tube 16 is a standard luer needle hub 48 which allows quick connection to a vacuum source in the operating room. Leads 18, 20 are terminated in a plug 50 which is adapted to be plugged into a device (not shown) for transmitting signals to the doppler flow transducer and for analyzing the return signals coming therefrom.

In operation, the device is placed over the particular vessel desired to be analyzed. FIG. 2 illustrates the suction cup 12 placed in position over a vessel 52, which is embedded within the tissue 54 of the organ in question which would be the heart, in the case of coronary bypass surgery. Needle hub 48 is connected to a vacuum source and the air is drawn outwardly from beneath suction cup 12 so as to force suction cup 12 into a flattened condition such as shown in FIG. 3. In this condition, the lens 42 of transducer assembly 14 is placed in forced contact with the surface of the tissue 54 surrounding vessel 42. In some cases, it may be possible to place lens 42 in direct contact with the vessel, but it is not absolutely necessary so long as there is a path of conductivity for sound from the transducer 26 through the lens 42 to the vessel 52.

An electrical signal is then introduced to transducer 26 through leads 18, 20. The signal is carried from leads 18, 20 to half circle plates 34, 36 which insure that the signal is spread over the entire upper surface of crystal disc 28. Disc 28, being formed of a piezoelectric material, reacts to the electrical signal by creating a sound impulse which is transmitted through lens 42 to vessel 52. The sound signal creates certain seconary sound signals or echos which return to crystal 28 via lens 42. Crystal 48, being of a piezoelectric material, responds to the secondary sound signals by creating a corresponding electrical signal which is picked up by half circle plates 34, 36 and is transmitted through leads 18, 20 to the electrical equipment (not shown) for analyzing the circuit.

In order to analyze the velocity of the fluid passing through vessel 52, it is first necessary to analyze the signals during a time when the vessel is operating in its normal condition. The second step is to measure the characteristics of the velocity of fluid flow through the vessel when the vessel is artificially occluded. This is usually accomplished with forceps to shut off the flow of fluid in the vessel. The third step in the analyzing of the flow characteristics of the vessel is to release the temporary blockage of the vessel and measure the velocity of fluid flow therein after the temporary occlusion is released.

Referring to FIG. 6, a velocity curve for a badly occluded vessel is shown. Portion A of the curve shows the magnitude of velocity prior to the temporary occlusion. Portion B of the curve shows the characteristic of the velocity of fluid flow within the vessel during the time of temporary occlusion. Portion C of the curve shows the characteristic of fluid flow after the temporary occlusion has been removed. In a vessel which is badly occluded, there is little change between portion A and portion C of the curve.

FIG. 7 shows a curve typical of a normal, healthy vessel which is not occluded. Portion D of the curve shows the velocity characteristics prior to the temporary occlusion. Portion E shows the characteristic during the temporary occlusion, and portion F shows the characteristics immediately after the temporary occlusion is removed. As can be seen, the velocity of fluid flow increases dramatically after the occlusion is removed to a magnitude which is substantially greater than prior to the temporary occlusion. As can be seen, portion F of the curve jumps up dramatically and then slowly recedes back to the original level shown in D.

Thus, in a matter of 2 to 20 seconds, it is possible to take a reading such as shown in FIGS. 6 or 7, and by the nature of the reading, tell whether or not there is serious occlusion of a vessel.

When the measurements have been taken which are desired, the vacuum is released from beneath the suction cup 12 and the device may be lifted up without harming the tissue surrounding the vessel.

The surgeon can place the suction cup at any desired location, and because the measurement takes only a matter of from approximately 2 to 20 seconds, it is possible to take several readings at various locations in order to isolate the badly occluded vessels surrounding the heart. The device may be used not only on the larger main coronary arteries, but also may be used on many of the smaller branches and therefore gives the physician a more precise analysis of the particular functioning of each of the various branches of the coronary arteries. The device has been found to cause no identifiable harm during the operation. For example, when the wires to the doppler probe were attached to the heat of an experimental animal and excited for several minutes, no changes in cardiac rhythm occurred. From this it was deduced that the small current required to operate the doppler had little or no measurable effect in the cardiac rhythm. Furthermore, in numerous instances cardiac tissues have been obtained from sites below the doppler probes, and have failed to show any tissue damage that could be detected by microscopy.

The device has been found to be highly reliable, and produces readings which closely correlate to the readings obtined with prior art methods for measuring the velocity and flow characteristics of the coronary arteries. The primary advantage of the present device over previous devices is that it can be done quickly with a minimum of damage or trauma to the artery or the tissues surrounding the artery. The device is simple and easily sterilized. It is economical to manufacture and reliable in operation. Thus, it can be seen that the device accomplishes at least all of its stated objectives.

What is claimed is:

1. A device for sensing the velocity of fluid flow to human and animal vessels, said device comprising:
   a cup means having a concave undersurface and being made of a flexible material which permits said cup means to be yieldably deflected into a substantially flat configuration;
   transducer means mounted on said undersurface of said cup means, said transducer means comprising a piezoelectric member having opposite surfaces, a pair of closely spaced sheet members being mounted on one of said opposite surfaces of said piezoelectric member;
   electrical lead means connected to said transducer means and leading from said transducer means to above said cup means for connection to a source of electrical signals;
   said lead means comprising a pair of electrical leads, each of which is in electrical connection with one of said sheet members;
   a vacuum conduit having a first end in communication with the space below said concave surface of said cup means and a second end adapted to be connected to a vacuum source for drawing air from beneath said cup means.

2. A device according to claim 1 wherein said cup means is comprised of dielectric material.

3. A device according to claim 1 wherein a dielectric material surrounds said sheet members.

4. A device according to claim 3 wherein said dielectric material surrounding said sheet members has a portion thereof shaped into a lense.

5. A device according to claim 3 wherein said cup means has an outer peripheral edge lying in approximately a single plane, said sheet members lying in a second plane, said second plane being disposed at a predetermined angle with respect to said first plane.

6. A device according to claim 5 wherein said predetermined angle is between 15° and 60°.

7. A device for sensing the velocity of fluid flow in human and animal vessels, said device comprising:
   a cup means having a concave undersurface and being made of a flexible material which permits said cup means to be yieldably deflected into a substantially flat configuration;
   transducer means mounted on said undersurface of said cup means;
   electrical lead means connected to said transducer means and leading from said transducer means to above said cup means for connection to a source of electrical signals;
   a vacuum conduit having a first end in communication with the space below said concave surface of said cup means and a second end adapted to be connected to a vacuum source for drawing air from beneath said cup means;
   said transducer means comprising a pair of closely spaced sheet members constructed of electrically conductive material,
   said lead means comprising a pair of electrical leads, each of which is in electrical connection with one of said sheet members;
   said transducer means further comprising a piezoelectric disc having opposite disc surfaces, said sheet members being mounted on one of said opposite surfaces of said disc.

8. A device for sensing the velocity of fluid flow in human and animal vessels, said device comprising:
   a cup means having a concave undersurface and being made of a flexible material which permits said cup means to be yieldably deflected into a substantially flat configuration;
   transducer means mounted on said undersurface of said cup means;
   electrical lead means connected to said transducer means and leading from said transducer means to above said cup means for connection to a source of electrical signals;

a vacuum conduit having a first end in communication with the space below said concave surface of said cup means and a second end adapted to be connected to a vacuum source for drawing air from beneath said cup means.

said transducer comprising a pair of closely spaced sheet members constructed of electrically conductive material;

said lead means comprising a pair of electrical leads, each of which is in electrical connection with one of said sheet members;

a dielectric material surrounding said sheet members;

said sheet members being in the shape of a half circle and each having a straight edge corresponding to the diameter of said circle, said straight edges of said two half circles being in parallel spaced apart relationship.

9. A method for sensing the velocity of fluid flow in an elongated animal vessel, said method comprising:
placing a flexible suction cup over said vessel, said suction cup having a doppler flow transducer on its under surface positioned in vertical alignment over said vessel;
attaching said transducer to the outer surface of said vessel by withdrawing the air from beneath said suction cup so that said suction cup collapses toward said vessel thereby bringing said transducer into sound transmitting continuity with the upper exterior surface of said vessel;
introducing a first electrical signal to said transducer whereby said transducer transmits a sound signal into said vessel;
using said transducer to sense the secondary sounds within said vessel created by said sound signal and to convert said sensed secondary sounds into a return electrical signal;
carrying said return electrical signal to means for analyzing said signal.

10. A method for sensing the velocity of fluid flow in an elongated animal vessel, said method comprising:
placing a flexible suction cup over said vessel, said suction cup having a doppler flow transducer on its under surface positioned over said vessel;
attaching said suction cup over said vessel by withdrawing air from beneath said cup to collapse said cup and press said transducer against said vessel;
closing off the fluid flow through said vessel;
transmitting first electrical signal to said transducer whereby said transducer will create a first sound signal to said vessel;
using said transducer to receive a first return sound signal from said vessel created in said vessel in response to said first sound signal;
using said transducer to convert said first return sound signal to a first return electrical signal;
conveying said first return electrical signal to analyzer means;
opening up said vessel to fluid flow;
transmitting a second electrical signal to said transducer whereby said transducer will create a second sound signal to said vessel;
using said transducer to receive a second return signal created in said vessel in response to said first sound signal, whereby said transducer will convert said second return sound signal to a second return electrical signal;
analyzing said second return electrical signal and comparing it to said first return electrical signal.

11. A method according to claim 10 comprising measuring the velocity of said fluid in said vessel prior to closing off the fluid flow through said vessel by transmitting an initial electrical signal to said transducer to cause an initial sound signal, using said transducer to receive an initial return sound signal from said vessel, using said transducer to convert said initial return sound signal to an initial return electrical signal, and conveying said initial return electrical signal to analyzer means.

12. A device for sensing the velocity of fluid flow in human and animal vessels, said device comprising:
transducer means comprising a sheet member made of piezoelectric material and having a first surface and an opposite second surface, and a pair of electrically conductive members attached to one of said first and second surfaces of said sheet member, said electrically conductive members being free from electrical connection to one another;
first electrical lead means connected to one of said electrically conductive members;
second electrical lead means connected to the other of said electrically conductive members,
support means carrying said transducer means and adapted to place said transducer means in sound transmitting continuity with one of said vessels;
said support means comprising a cup means having a concave undersurface and being made of a flexible material which permits said cup means to be yieldably deflected into a substantially flat configuration;
said transducer means being mounted on said undersurface of said cup means;
means for withdrawing air from beneath said cup means.

13. A device according to claim 12 wherein said sheet member is supported by said support means in a position wherein said first surface of said sheet member is presented away from said one vessel when said transducer means is in sound transmitting continuity therewith.

14. A device according to caim 13 wherein said sheet member comprises a circular disc.

15. A device according to claim 14 wherein said conductive members each comprise a thin conductive film in covering engagement with a portion of said one side of said sheet member.

16. A device according to claim 15 wherein each of said conductive members is shaped in an approximate half circle superimposed over approximately one half of said first surface of said disc, said two conductive members being spaced apart from one another adjacent the diameters of said half circular shapes.

17. A device for sensing the velocity of fluid flow in human and animal vessels, said device comprising:
a cup means having a downwardly presented concave undersurface and being made of a flexible material which permits said cup means to be yieldably deflected into a substantially flat configuration;
transducer means mounted on said undersurface of said cup means, said transducer means comprising a piezoelectric member having a pair of electrically conductive sheet members mounted on the outer surface thereof,
said transducer means being embedded within a dielectric sound transmitting material which forms a protrusion extending downwardly from said concave undersurface of said cup means;
a pair of electrical leads extending from outside of said cup means through said cup means and said electric sound transmitting material of said protrusion and into electrical contact with said conductive sheet members;
vacuum means for withdrawing air from beneath said cup means.

* * * * *